(12) United States Patent
Brewster et al.

(10) Patent No.: US 8,865,088 B2
(45) Date of Patent: Oct. 21, 2014

(54) LIQUID SAMPLE ASSAY DEVICE

(75) Inventors: Barry Sinclair Brewster, Royston (GB); Susan Catrin Day, Brampton (GB); Peter John Skelly, Brickhill (GB); Jill Crawford, Newton (GB)

(73) Assignee: Alere Switzerland GmbH, Zug (CH)

( * ) Notice: Subject to any disclaimer, the term of this patent is extended or adjusted under 35 U.S.C. 154(b) by 1576 days.

(21) Appl. No.: 10/495,714

(22) PCT Filed: Jan. 9, 2003

(86) PCT No.: PCT/GB03/00056
§ 371 (c)(1),
(2), (4) Date: May 14, 2004

(87) PCT Pub. No.: WO03/058245
PCT Pub. Date: Jul. 17, 2003

(65) Prior Publication Data
US 2004/0253142 A1  Dec. 16, 2004

(30) Foreign Application Priority Data
Jan. 9, 2002  (EP) .................................. 02250121

(51) Int. Cl.
*G01N 33/00* (2006.01)
*G01N 33/543* (2006.01)
*G01N 33/76* (2006.01)
*G01N 33/94* (2006.01)
*G01N 33/558* (2006.01)

(52) U.S. Cl.
CPC .......... *G01N 33/94* (2013.01); *G01N 33/54366* (2013.01); *G01N 33/76* (2013.01); *G01N 33/558* (2013.01)

USPC .......... 422/401; 422/402; 422/408; 422/420; 422/421; 422/68.1

(58) Field of Classification Search
USPC ........ 422/50, 55, 56, 57, 68.1, 401, 402, 408, 422/420, 421
See application file for complete search history.

(56) References Cited

U.S. PATENT DOCUMENTS

| | | | |
|---|---|---|---|
| 3,811,840 A | | 5/1974 | Bauer et al. |
| 4,677,079 A | | 6/1987 | Langhals |
| 5,075,078 A | * | 12/1991 | Osikowicz et al. ........... 422/420 |

(Continued)

FOREIGN PATENT DOCUMENTS

| | | |
|---|---|---|
| EP | 0 560 411 | 9/1993 |
| EP | 0 291 194 | 2/1994 |

(Continued)

OTHER PUBLICATIONS

International Search Report, PCT Application No. PCT/GB 03/00056, mailed Apr. 4, 2003.

(Continued)

*Primary Examiner* — Sam P Siefke
(74) *Attorney, Agent, or Firm* — Foley Hoag LLP

(57) ABSTRACT

Disclosed is an assay device for use in the determination of the presence of at least one analyte of interest in a liquid sample; the device comprising a reaction zone in which a reagent reacts with the analyte of interest and a bibulous member which, when contacted with the liquid sample, draws liquid therefrom towards the reaction zone; the bibulous member comprising means to change color when wetted by the sample.

19 Claims, 1 Drawing Sheet

(56) References Cited

U.S. PATENT DOCUMENTS

| | | | |
|---|---|---|---|
| 5,275,785 A | 1/1994 | May et al. | |
| 5,602,040 A | 2/1997 | May et al. | |
| 5,622,871 A | 4/1997 | May et al. | |
| 5,656,503 A | 8/1997 | May et al. | |
| 5,852,126 A | 12/1998 | Barnard et al. | |
| 5,922,612 A | 7/1999 | Alder et al. | |
| 6,187,598 B1 | 2/2001 | May et al. | |
| 6,194,224 B1 * | 2/2001 | Good et al. | 436/518 |
| 6,228,660 B1 | 5/2001 | May et al. | |
| 6,235,539 B1 | 5/2001 | Carpenter | |
| 6,352,862 B1 | 3/2002 | Davis et al. | |
| 6,572,822 B2 * | 6/2003 | Jurik et al. | 422/56 |
| 2001/0008774 A1 | 7/2001 | May et al. | |
| 2001/0041368 A1 | 11/2001 | May et al. | |
| 2002/0044891 A1 | 4/2002 | Miller et al. | |

FOREIGN PATENT DOCUMENTS

| | | |
|---|---|---|
| GB | 6201689 | 7/1994 |
| JP | 6201689 | 7/1994 |
| JP | 2001-133455 A | 5/2001 |
| JP | 2001221798 A | 8/2001 |
| WO | WO 99 04256 | 1/1999 |

OTHER PUBLICATIONS

European Communication for Application No. 03700843.0 dated Apr. 17, 2013.

Bicomponent Fiber, Definition of; Fibersource Home, [http://www.fibersource.com/f-tutor/bicomponent.htm] (p. 1 of 1) (Aug. 23, 2013).

Bicomponent Fiber, Definition of; McGraw-Hill Science & Technology Dictionary; [http://www.answers.com/topic/bicomponent-fiber] (2003).

He, Feng. "An Investigation of the Interfacial Microstructure and Properties of Side-by-Side Bicomponent Polymer Fibers," Thesis submitted to the Graduate Faculty of North Carolina State University, (Abstract) 2 pgs. (2010).

Hedge, Raghavendra R., et al. "Bicomponent Fibers," [http://www.engr.utk.edu/mse/Textiles/Bicomponent%20fibers.htm] (pp. 1-8) (Apr. 2004.).

Porter, K. "Fibers, Multicomponent," ICI Fibres; pp. 473-474 in Kirk-Othmer in Concise Encyclopedia of Chemical Technology, Wiley Interscience (1985).

* cited by examiner

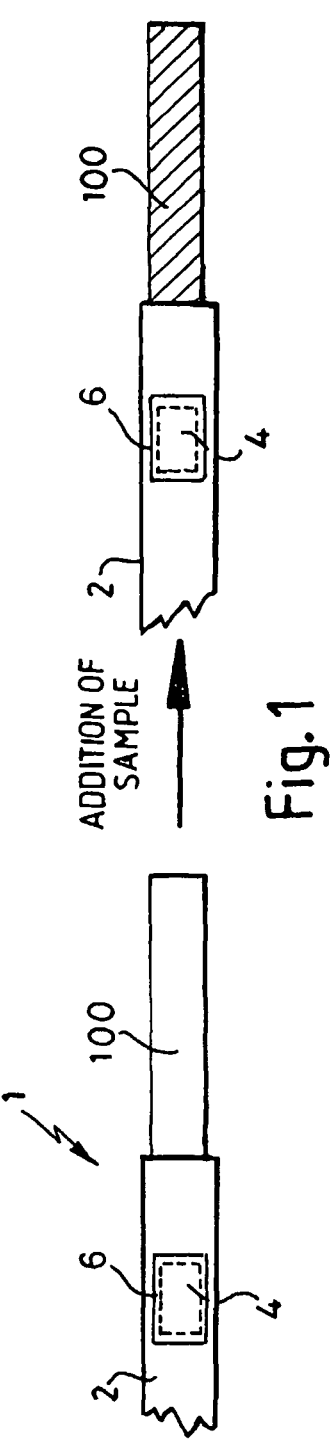
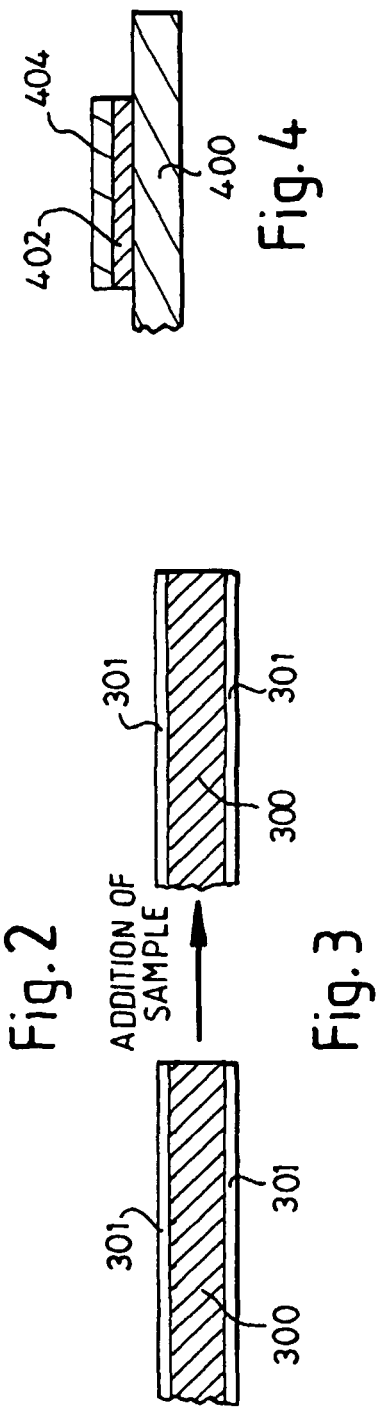
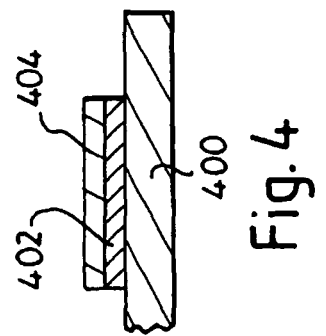

LIQUID SAMPLE ASSAY DEVICE

The present application relates to the field of assay devices for measuring the presence and/or amount of at least one analyte in a liquid sample.

BACKGROUND TO THE INVENTION

A number of assay devices for use in the measurement of one or more analytes in a liquid sample are known. Some of these are complex devices for use by trained personnel; for example, sampling devices for industrial liquids, water etc. or laboratory tests on blood, urine and the like. However, an important category of assay devices are intended for home use by consumers. It is important that assay devices are as simple to operate and interpret as possible, particularly when intended for home use, and it is also important that users have confidence in the reliability of the results.

Examples of such home monitoring assay devices include pregnancy test kits, for example, the Clearblue test from Unipath, England (Clearblue is a registered Trade Mark) and as described in EP 291194 and EP 560411. Home pregnancy tests typically determine the amount of the hormone human chorionic gonadotrophin (hCG) in a urine sample, and normally provide a visual indication as to whether a subject is pregnant.

Some assay devices, such as the Clearblue® test, are self-contained disposable devices. Other disposable assay devices, usually containing one or more reagents to react with an analyte in a urine sample, are used in conjunction with other devices, for example non-disposable electronic meters. This category of product includes the Persona® monitor, from Unipath, which indicates fertile and non-fertile days in the menstrual cycle, and the Clearplan® test kit, also from Unipath, which identifies the most likely time of ovulation in a cycle. Both of these products monitor hormone concentrations in daily urine samples and comprise electronic measuring and/or recording devices and separate, disposable, assay devices for taking an individual urine sample and carrying out the relevant assay.

These assay devices have wicks for taking up a urine sample and delivering it to a reaction zone where analyte of interest in the sample (if any) reacts with one or more reagents, such as labelled antibodies.

When using a wick to take up a urine sample, it is often hard to see that a sample has been taken up correctly or that sufficient sample has been applied to the wick. More specifically, with this type of device, the urine sample is often obtained directly from the urine stream and so it is difficult for the user to see or control the sampling operation and therefore have confidence that the sampling operation has been performed correctly. It would be advantageous to mitigate this potential concern and reassure users that the device has been correctly operated.

U.S. Pat. No. 3,811,840 discloses a "dip-and-read" type assay device comprising a bibulous wick for immersion in a liquid sample. The wick may comprise a chemical indicator which gives a signal after a predetermined time "to give a visual indication of saturation of the wick to the extent desired". The document teaches the importance of placing the chemical indicator downstream of the detection zone, so as to ensure that the user is instructed to remove the assay device from the sample only once sufficient saturation of the wick has taken place. Thus, there is a time delay between contacting the assay device with the liquid sample and the appearance of the visual indication. For example, in the embodiment illustrated in FIG. 8 of U.S. Pat. No. 3,811,840, a fluid sensitive chemical is deposited downsteam of the detection zone.

Any alteration made to conventional assay devices should preferably fulfil commercial criteria of cost and user acceptance, ready disposability, safety and long term stability, and should not compromise other characteristics of the assay devices.

SUMMARY OF THE INVENTION

According to a first aspect of the present invention there is provided an assay device for use in the determination of the presence of at least one analyte of interest in a liquid sample; the device comprising a reaction zone in which a reagent reacts with the analyte of interest and a bibulous member which, when contacted with the liquid sample, draws liquid therefrom towards the reaction zone; the bibulous member comprising means to change colour when wetted by the sample.

The change of colour by the colour change means provides a visual indication to a user that they have successfully contacted the liquid sample with the bibulous member. Therefore, this invention gives a positive indication that the assay device has been used correctly, giving the user confidence in the results. This is particularly important if the liquid is urine and the assay device is designed so that a user urinates directly on the bibulous member as, otherwise, the user would have no visual indication that they have done this successfully, since urine generally is not strongly coloured.

It will be noted that, since the bibulous member is upstream of the reaction zone, the bibulous member will generally undergo a colour change before the reaction of the reagent with the analyte of interest. In particular, in preferred embodiments the bibulous member undergoes a colour change substantially immediately upon contact with the liquid sample. For present purposes "substantially immediately" means within 10 seconds of initial contact with the liquid sample, more preferably within 5 seconds, and most preferably within 2 seconds of initial contact. Accordingly, in preferred embodiments the present invention provides an assay device which allows the user thereof to determine whether they have correctly applied a sample to the assay device at the time of sampling (i.e. within 10 seconds, more preferably within 5 seconds, and most preferably within 2 seconds of initial contact with the sample).

The means to change colour may be adapted to change colour when sufficient sample has been applied to the wick to generate a meaningful assay result.

Optionally, the assay device comprises a separate positive control which indicates that not only has sufficient liquid been taken up, but that at least one additional aspect of the assay device has worked correctly. For example, a positive control showing that an analyte-specific binding reagent carried by the liquid sample has reached a point at or past the reaction zone, may be incorporated.

Typically, the bibulous member consists of a series of fibres drawn together in parallel to form an open wick with some mechanical integrity due to bonding between the fibres, with the space between the fibres acting to form channels which draw up the urine. Suitable fibres include polyester, polyamides such as nylons, bicomponent fibres such as polyethylene/polyester, nylon/polyester and the like. Bicomponent polyethylene/polyester fibres typically comprise a polyester central core with an external sheath of polyethylene. Inherently hydrophobic fibres such as polypropylenes could also be used provided they are water wettable or, if necessary, are rendered water wettable by other components such as surfactants, hydrophilic polymers etc. Any wettable fibre is, in principle, usable.

Fibres can be formed into a bibulous member by a variety of processes, such as annealing to partially melt the surface/sheath region and cause interpenetration of the polymer chains, which set on cooling. Alternatively, adhesives, such as latex adhesives, may be used.

Woven or non-woven materials can form the bibulous member. Non-woven fibre mat materials are used e.g. in Persona® from Unipath, Bedford, England. These bibulous members comprise randomly aligned fibres in a layer on a support. Transorb®, available from Filtrona Richmond, Inc. Virgina, USA, is a suitable example of a woven material commonly used as a bibulous member in lateral flow devices such as pregnancy and ovulation tests and in other applications requiring collection and transfer of sample liquids or reagents. Preferably, the bibulous member comprises a heat-bonded polyester/polyethylene bicomponent fibre. The bibulous member may be elongate and substantially flat, in which case one flat surface may be covered in a liquid impermeable layer. We have found that, even if the user urinates on a bibulous member having a liquid impermeable layer on one flat surface, liquid can still be taken up correctly.

As an alternative to a wick formed of woven or non-woven fibres, the bibulous member may comprise a flow channel formed by, for example, an array of microchannels.

The means for changing colour may, for example, be all of, or one or more component parts of, the bibulous member; a material impregnated within the bibulous member; a layer around or within the bibulous member; or a label on the bibulous member. The material or polymer used to form the bibulous member may itself be a substance which undergoes a colour change (rather than comprise a colour change species trapped within or bound to the fibres of the bibulous member).

In one embodiment, the means for changing colour may comprise a chemical species that changes colour in response to a property of the liquid sample; for example, a solvatochromic dye, such as Reichardt's dye. Another example is a pH indicator, such as bromocresol green (acid form), phloxine B, quinalidine red, bromophenol blue (acid form), bromochlorophenol blue (acid form), ethyl violet, Nile blue A (alkaline form), water blue (alkaline form) or malachite green (alkaline form). Appropriate pH indicators can be selected bearing in mind the likely pH range of the liquid sample and the colour change properties of the indicator. An indicator is typically immobilised with a buffer or other substance, e.g. acid or alkali, to control its initial pH and so its initial colour. pH indicators are of particular benefit when the liquid sample is urine. The pH of urine is normally in the range 4.7-8, so an indicator that undergoes a colour change upon entry into this range (whether from above or below) would be useful in such embodiments.

Screened indicators, which comprise two or more dyes mixed together, may also be used and these have the benefit of changing colour over a relatively narrow pH range. For example, a mixture of xylene cyanol FF and methyl orange. Advantageously, such indicators may have a grey point, i.e. be grey/colourless at a particular composition/pH. When immobilised at the grey point on the bibulous member, the bibulous member appears colourless but then displays a strong colour on addition of urine or other appropriate liquid samples.

The means for changing colour may comprise one or more chemical species that undergo a reversible or irreversible reaction with, or a reaction catalysed by, a substance or substances present in the sample. For example, chromoreactants, particularly those such as 4-(N,N-dioctylamino) 4'-trifluoroacetylazobenzene ($ETH^T$ 4001), which comprise trifluoroacetyl groups and react with amines, such as those normally present in urine.

The chemical species may be immobilised within a polymer which entraps the chemical species, for example, poly 2-hydroxy ethyl methacrylate (poly(HEMA)) or poly hydroxy propyl methacrylate (poly(HPMA)). Poly(HEMA) may be formed from 2-hydroxy ethyl methacrylate and an initiator, such as 2,2' azobis-(2-methylpropionitrile) (AZBN) (all are available from Aldrich Chemical Company (Gillingham, Dorset, England)). An uncrosslinked polymer, e.g. a homopolymer of HEMA may be used to entrap the chemical species. However, it is preferred to form a crosslinkable polymer, such as a copolymer of HEMA with glycidyl methacrylate and methacrylic acid and then to coat the fibres with this crosslinkable polymer and the chemical species. Thereafter, the solvent is evaporated and then the monomer is crosslinked in situ, forming an insoluble polymeric mesh and trapping the chemical species. The epoxy rings from glycidyl methacrylate undergo a crosslinking reaction with the carboxylic acid groups from methacrylic acid when heated to 80° C. Crosslinking helps retain chemical species both by physical hindrance and by limiting the swelling of the polymer in water.

Alternative polymers can readily be chosen by one skilled in the art; for example, substituted polyamides including those in which a substantial proportion of the amide groups are substituted with methyl methoxy groups, such as those sold under the name Elvamide® nylon multipolymer resins by Du Pont. (See "Polyamides of enhanced solubility", page 415, "Plastics Materials" by J. A. Brydson (Butterworths, 1975)). Another possible polymer is the copolyamide Griltex IG® sold by EMS-Grilon, Stafford, United Kingdom.

The polymer containing the chemical species may be introduced to the bibulous member and then dried. Chemical species may be covalently linked to polymer or directly to the bibulous member instead or as well as being immobilised by entrapment. For example, $ETH^T$ 4012 has methacrylate groups and may be copolymerised into polymer for coating the bibulous member. Alternatively, a chemical species may be immobilised in the bibulous member by the formation of an ion pair: if a counter ion with large hydrophobic groups is added to an ionic pH indicator or other suitable species, an internal salt will result which is hydrophobic and hence insoluble in aqueous solutions.

Typically the bibulous member may be formed using bicomponent fibres, in which a core fibre is wholly or partially surrounded by a sheath of a different material. A suitable colour change species may be trapped, immobilised or otherwise retained in the core and/or in the sheath of a bicomponent fibre. Alternatively, the colour change chemical species may be an integral part of the chemical structure of the fibres e.g. as part of a side chain of a polymer which forms a mono- or bicomponent fibre.

In an alternative embodiment, the means for changing colour comprises a coloured material at least partially covered by a substantially opaque layer that becomes sufficiently clear to enable the coloured material to be seen in response to the presence of liquid. The coloured material may be the bibulous member, in which case the bibulous member may comprise coloured polyester/polyethylene fibres. Colouring can be achieved using fibres incorporating a coloured compound when manufactured or by subsequently immersing the bibulous member, once manufactured, in dye. For example, polyester coloured fibres can be coloured with solvent blue 36 in toluene. The coloured material may be a label applied to the bibulous member. The coloured material may be a layer impregnated within or applied to the bibulous member, for example an acetate strip.

A particular benefit of this configuration is that any visual indication can be provided underneath the initially opaque layer; for example, a block of a single colour, a symbol or writing. The substantially opaque layer may be selected from a group comprising: sugar paste (e.g. glucose paste); nitrocellulose membranes, with or without a clear laminate backing (available from Millipore Corporation, Bedford, Mass., USA or Schleicher & Schuell GmbH, Dassel, Germany); a nylon microporous membrane (such as Novylon® L-series Nylon 6,6 membranes available from Cuno, Inc. of Meridian Conn., USA) and Whatman No. 1® filter paper (Whatman International Ltd., Maidstone, Kent, United Kingdom).

The means for changing colour may comprise a pH paper in fluid contact with the bibulous member. For example the means for changing colour may be a pH paper which changes colour when urine is applied. A buffer, such as Tris may be present in the bibulous member. The buffer dissolves in the presence of aqueous sample, changing the pH of the aqueous sample and so the colour of the pH paper.

Preferably, the assay device is disposable.

The device preferably comprises one or more reagents that react specifically with the analyte of interest. The device may also comprise means for providing a visual indication of the results of the assay.

The assay device may be adapted to co-operate with a measuring device. The measuring device may be an electronic reader that measures and/or records and/or interprets the results of the tests.

The assay device may be used to give a qualitative result (e.g. the presence or absence of the analyte of interest in the sample), or a quantitative result (i.e. a measure of the amount of the analyte of interest in the sample), and the term "presence of an analyte" should accordingly be construed as referring to presence and/or amount of an analyte.

Preferably, the analyte of interest is a hormone and the assay device tests for a condition associated with that hormone; for example, in a pregnancy test, the analyte of interest may be hCG. Alternatively the analyte of interest may be a drug of abuse, such as an opiate, amphetamine or cocaine. It will be apparent to those skilled in the art that the assay device may be used to test for the presence of more than one analyte of interest in a sample. For example, two different analyte-specific binding reagents may be provided on the device, each specific for a respective analyte of interest.

In one preferred embodiment, the assay device comprises a hollow casing constructed of moisture-impervious solid material and containing a dry porous carrier which communicates directly or indirectly with the bibulous member which protrudes from the casing such that a liquid sample can be applied to the bibulous member and carried to the porous carrier, the device also containing a labelled specific binding reagent for an analyte which labelled specific binding reagent is freely mobile within the porous carrier when in the moist state, and unlabelled specific binding reagent for the same analyte which unlabelled reagent is permanently immobilised in a detection zone on the porous carrier and is therefore not mobile in the moist state, the relative positioning of the labelled reagent and detection zone being such that the liquid sample applied to the device can pick up labelled reagent and thereafter permeate into the detection zone, the device incorporating means enabling the extent (if any) to which the labelled reagent becomes bound in the detection zone to be observed.

Preferably, the label is a particulate direct label, such as coloured latex particles having a maximum diameter of not greater than about 0.5 microns. Preferably also, the labelled reagent is contained in a first zone of the dry porous carrier, and the unlabelled reagent is immobilised in a detection zone spatially separated from the first zone, the two zones being arranged such that liquid sample applied to the porous carrier can permeate via the first zone into the detection zone.

The assay device may be supplied with a cap, covering the bibulous member, to be removed before use and optionally replaced.

According to a second aspect of the present invention there is provided a method of determining the presence of at least one analyte in a liquid sample, the method comprising the steps of: contacting an assay device in accordance with the first aspect of the invention with the liquid sample; and observing the assay result.

An illustrative example of the present invention will now be described with reference to the following figures in which:

FIG. 1 is a schematic illustration of part of an assay device having a colour-changing wick, in plan view;

FIG. 2 is a schematic cross-section through a coloured wick with a soluble coating;

FIG. 3 is a schematic cross-section through a coloured wick with a cover layer which becomes transparent on wetting; and FIG. 4 is a schematic cross-section through a wick with a colour changing layer thereon.

EXAMPLE 1

Assay device 1 is part of a test kit, suitable for home use in determining whether a female subject is pregnant by analysing whether hCG is present in their urine. Assay device 1 comprises a casing 2 having a reaction zone 4 visible through a result window 6. A bibulous member, in the form of a wick 100 protrudes from the casing 2.

Wick 100 is manufactured from heat-bonded polyester/polyethylene bicomponent fibres of 31.5±7% micron diameter and has been pretreated with the detergent Tween-20 to make it more hydrophilic and reduce the binding of analyte (here, hCG) to the wick.

Wick 100 has been treated with bromocresol green, a pH indicator functioning as a means for changing colour. Bromocresol green is applied in a matrix of cross-linkable poly hydroxy ethyl methacrylate (poly(HEMA)) copolymerised with glycidyl methacrylate and methacrylic acid. A suitable bromocresol/poly(HEMA) solution can be made by dissolving about 20.19 grams of poly(HEMA) copolymer in 200 ml ethanol and stirring with the application of heat until all the poly(HEMA) copolymer has dissolved. Thereafter, 1.84 g of bromocresol green is added to the polymer/ethanol mix which is stirred until the bromocresol green has dissolved. The solution is then acidified with a few drops of concentrated hydrochloric acid to place the indicator into its acidic form. The resulting solution is then added to the wick by dipping the wick into the solution until the wick is completely coated. The polymer is thus distributed throughout the wick, coating internal surfaces. The ethanol is then removed, by spin drying the wick slowly overnight, then placing the wick under vacuum at approximately 60° C. overnight. Next, the wick is raised to around 80° C. to cross-link the poly(HEMA) copolymer strands. This leaves the poly(HEMA)/dye mix coated to the wick and gives the wick 100 an initially yellow or yellow/orange colour.

The assay device is operated by urination on the wick 100. Alternatively, the wick 100 may be dipped into a urine sample. Urine has a normal pH range of 4.7-8. (H. A. Harper, "Review of Physiological Chemistry", Lange 1969, pp 413). Bromocresol green has a pKa/b of 4.70 and a colour transition range from pH 3.8 (yellow/orange) to 5.4 (green/blue).

When urine contacts the wick 100, the relatively alkaline pH causes the bromocresol green to change from an initial yellow/orange colour to a green/blue colour. This enables a user to see clearly that urine has been added to the assay device.

As with known assay devices, the urine is then wicked into the body of the assay device, by the wick. The reaction zone 4 provides a visual indication of pregnancy by known immunoassay means; for example, as described in EP 0 291 194 or EP 0 560 411 in which blue latex bead-labelled mouse anti-hCG antibodies are present in the device and are carried along a nitrocellulose strip, binding to any hCG which is present. The nitrocellulose strip has a reaction zone having immobilised anti-hCG antibodies which form a sandwich assay complex with hCG and labelled anti-hCG antibodies, giving a visible indication of the presence of hCG. These documents also teach the concept of a control zone, comprising anti-mouse antibodies, which traps the latex beads irrespective of whether they have bound hCG, giving a visible indication that all steps of the assay have functioned correctly.

EXAMPLE 2.0

As well as bromocresol green, other pH indicators may readily be substituted by one skilled in the art. Both acid and alkaline forms of indicators may be used. For example, malachite green hydrochloride can be immobilised in pH 14 buffer and undergoes a clear to blue colour transition when urine is added. Phloxine B is immobilised below pH 2.2, where it is initially colourless and then changes colour to pink when urine is added. In selecting an alternative indicator, a number of parameters must be considered:
(i) The pKa/b of the indicator. This should preferably be in the range 0-5 or 8-14, more preferably in the range 2-4.75 or 8.5-10
(ii) The colour change should be unambiguous, changing to a strong, bright colour. Desirably, it may be from white or clear to blue. Ideally it will avoid colours such as yellow, brown and red that are not perceived as pleasant.
(iii) The indicator should not interfere with the functioning of the assay or the wick.
(iv) The colour change should persist sufficiently long, such as at least 10 minutes, or preferably be irreversible, so that a user can continue to see that the test has been performed correctly.
(v) The indicator should be stable for at least two years under typical shop and home storage conditions.
(vi) If intended for home use, the assay device must be safe to handle by the user and be safe for disposal at home.

EXAMPLE 2.1

This example relates to a general method for preparing a bicomponent bibulous wick member for use in an assay device in accordance with the invention.
1. A bicomponent wick is prepared having a core of polyester surrounded by a sheath of Nylon. The Nylon sheath is optionally treated with a surface active agent (such as Tween 20 or Triton X-100 or the like) to optimise its ability to be wetted by aqueous solutions. The wicks are then immersed in a dilute solution (0.05 gms l$^{-1}$) of phloxine B in deionised water. The water swells the sheath and the dye ingresses into the fibres with the water and, without being bound by any particular theory, the inventors hypothesise that hydrogen bonding may be responsible for retention of the dye by the fibre.
2. After 5 minutes' immersion the wicks are withdrawn from the phloxine B solution and immediately washed in deionised water until the wash liquor shows no sign of any dissolved dye. The wicks are stained pink in colour.
3. The pink wicks are immersed in an aqueous solution buffered to pH1 (Normadose pH1, Prolabo), which turns the wicks white (converts the phloxine B to its acid form).
4. When the wicks are completely white they are removed from the buffer and dried. Excess buffer can first be removed (by spinning, for example) and drying completed by heating under vacuum. The dried wicks may be stored with a desiccant until required.

In the above process, the colour change species (phloxine B) is incorporated subsequent to manufacture of the wick. As an alternative, it should be possible to incorporate the colour change species into the wick during its manufacture. In particular, a bicomponent wick could be made using a polyester core (for example) and a Nylon sheath as above, except that the colour change species or indicator (together with any optional surfactant, if desired) is incorporated into the Nylon by melt processing prior to coating onto the polyester core.

EXAMPLE 2.2

Instead of a single pH indicator, it may be desired to use a dye in combination with an indicator or to use two or more dyes in conjunction. A mixture of an indicator and a dye is known as a "screened indicator". For example, methyl orange (a colour changing indicator) and xylene cyanol (a blue dye), when mixed and immobilised in poly(HEMA) as before, give a screened indicator system which, in moving from acidic to basic conditions, changes from green to magenta. A suitable indicator can be formed from 0.14 g of xylene cyanol FF (Aldrich) and 0.1 g of methyl orange in 100 ml distilled water. This solution is magenta when acidified to pH 2 and green when taken to pH 6. This is because methyl orange is red in acid (pH3.2) and is yellow in base (pH4.4) and the xylene cyanol FF is blue independent of pH.

EXAMPLE 2.3

Some screened indicator systems display a "grey point" when mixed in the correct proportions, including the methyl orange/xylene cyanol combination of Example 2.1. In such proportions, they pass from one colour in acidic conditions to a second colour in basic conditions with an intermediate grey colour. For example, the above methyl orange/xylene cyanol solution can be brought to a grey point by titrating the acid form with dilute base to around pH3.8. By immobilising a screened indicator at its "grey point", a pH change in the presence of urine will cause the screened indicator to change to one of its colours. It can be important to take into account changes in the chemical environment on immobilisation and prepare a screened indicator preparation which is not at its grey point until it is actually immobilised in the wick.

EXAMPLE 2.4

Indicators can be replaced with solvatochromic dyes. These change colour according to the solvent in which they are dissolved, as they display pronounced changes in the wavelength of light absorbed or emitted with the polarity of the solvent. These wavelength changes can be either increases or decreases in wavelength. One option is Reichardt's dye which displays very strong negative solvatochromism. Reichardt's dye has the structure:

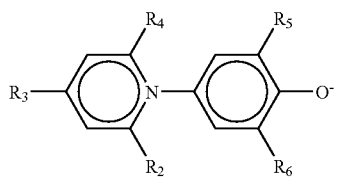

Reichardt's dye is added to a mixture of poly(HEMA)/ethanol until a strong blue/violet colour is observed. The mixture is stirred until the dye has dissolved. The resulting solution is blue/violet. The solution is then taken up into the wick and dried overnight, leaving a colourless wick.

EXAMPLE 2.5

Chromoreactands may be used as an alternative to indicators. A chromoreactand is used which undergoes a reaction with a component of the sample, for example amines in urine. As a consequence of these reactions, the wavelength of light absorbed/emitted by the chromoreactand changes. Suitable chromoreactands include those with trifluoroacetyl groups which react with alcohol, amine or water analytes to form diols, hemiaminal, hemiacetal or zwitterion groups which cause a change in absorbance characteristics.

A suitable chromoreactand is $ETH^T$ 4001, (4-N,N-dioctylamino) 4'-trifluoroacetyl azobenzene the structure of which is illustrated below. $ETH^T$ 4001 can be immobilised in poly(HEMA) as before.

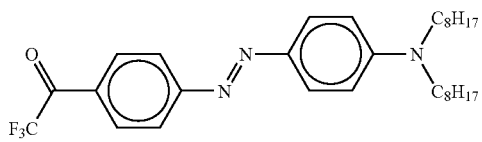

Reaction schemes for synthesising $ETH^T$ 4001 are to be found in the literature, e.g. "Development of Chromogenic Reactands for Optical Sensing of Alcohols", G. J. Mohr el al., "Sensors and Actuators B"49, 226-234 (1998). Reaction schemes for derivatives are described in "Reversable Chemical Reactions as the basis for optical sensors used to detect amines, alcohols and humidity", J. Mater. Chem. 2, 2259-2264 (1999) G. J. Mohr et al.

EXAMPLE 3

It will be apparent to one skilled in the art that the composition of poly(HEMA) can be modified to optimise immobilisation of any particular colour changing chemical. Other polymers can be selected by one skilled in the art to entrap or covalently immobilise the colour changing chemicals.

For example, the indicator phloxine B can be immobilised in Elvamide® polymer available from Du Pont. An appropriate wick can be prepared by dissolving 50 grams of Elvamide 8063® polymer in 450 grams of ethanol and stirring with the application of heat until all the Elvamide® polymer has dissolved. Thereafter, 0.04 grams of phloxine B are added to 100 ml of the Elvamide® polymer/ethanol mix which is stirred until the phloxine B has dissolved. The solution is then acidified with a few drops of concentrated hydrochloric acid to place the indicator into acidic form. The transition range of phloxine B is pH 2.2 (colourless)-3.3 (pink). The solution can then be added to the wicks by dipping the wicks into the solution until they are completely coated, as before. Ethanol can then be removed by spin drying the wick slowly overnight, then placing them under vacuum at approximately 60° C. overnight, as before.

Preferably the ethanolic solution of Elvamide also comprises an ethanol-soluble surfactant such as Tween 20, Triton X-100 or Tetronic 908. This renders the resulting wick more readily wettable by aqueous samples, with a shorter wicking time.

A suitable method for producing such a wick comprises the following steps:

1. Elvamide 8063 (60 gms), is dissolved in ethanol (840 mls), with stirring and heating in a jacketed reaction vessel until all the polymer has dissolved.
2. In a separate vessel phloxine B (0.6 gms), is dissolved in 100 mls of ethanol until the indicator has dissolved.
3. The phloxine B solution is added to the Elvamide solution with stirring, and cooled to room temperature.
4. This is followed by the addition of an amount of Tween 20, (2.4 gms), which is 4% by weight of the Elvamide polymer.
5. The resulting mixture is removed from the vessel and adjusted to pH 1 by the addition of concentrated hydrochloric acid. The solution becomes very pale.
6. The wick core fibres (e.g. polyester or the like) to be coated are placed in a disposable mesh bag and the end closed off.
7. The bag of wick cores is immersed in the solution for several minutes, with mild agitation, and air allowed to escape from the interior of the wicks.
8. The bag is removed from the solution, and the excess solution allowed to drip back into the pot.
9. The bag is then placed in a rotary evaporator flask, and the vacuum applied and spinning commenced.
10. The bath temperature of the rotary evaporator is slowly raised in stages from 30 degrees to 90 degrees, using the following cycle—30 minutes at 30° C., 30 minutes at 50° C., 30 minutes at 70° C., and finally raised to 90° C. (This gradual process results in efficient coverage of the wick fibres by a Elvamide/Tween 20/Indicator matrix, as confirmed by electron microscopy.)
11. The bag is removed and the colourless wicks retrieved. The wicks can then be used to assemble an assay device in a conventional manner. The inventors have used assay devices containing wicks prepared by the above method: when contacted with urine standards the wicks change colour from white to pink within a few (<5) seconds. The colour does not run into the reaction zone.

The amount of surfactant has to be optimised so that there is not too little as to have no effect on the wicking speed, but not too much that the polymer/surfactant matrix is too hydroscopic, and as a result allows leaching of the dye into the sample fluid. A preferred level is between 1 and 4% surfactant by weight of Elvamide polymer.

Without the presence of the surfactant the wicking times for the same polymer concentration and considerably longer, >20 seconds.

Yet a further variant is to use "thread bonding" in which a core fibre (such as polyester) is pulled through a bath of indicator or colour change species (e.g. phloxine B), and Elvamide™ solution or similar, with or without surfactant, to form a bicomponent fibre impregnated with phloxine B.

Example indicators which change colour from acidic to basic form in the presence of urine include: bromocresol green, acid form; quinaldine red; phloxine B; bromophenol blue, acid form; bromochlorophenol blue, acid form; and ethyl violet.

Example indicators which change colour from basic to acid in the presence of urine include the alkaline forms of Nile blue A, water blue and malachite green.

Polymers suitable for use in manufacture of wicks for use in the assay device of the invention include poly hydroxyl propyl methacrylate; and Elvamide 8061® and Elvamide 8063® both of which are alcohol soluble polyamides available from Du Pont®.

EXAMPLE 4.0

FIG. 2 illustrates a wick 200 formed from heat-bonded polyester/polyethylene bicomponent fibres which comprise a polyester core covered in a layer of polyethylene. The wick 200 is swollen in a toluene solution of a blue dye, solvent blue 36. Being a similar hydrocarbon, toluene swells polyethylene, and carries the dye into the polyethylene sheath at the same time. Removal of the solvent by rotary evaporation results in the solvent being removed faster than the higher molecular weight dye, ensuring that a significant proportion of blue dye is left behind encapsulated in the polymer. Excess dye on the surface of the wick can be removed by washing the wick in a solvent such as ethanol/water, which dissolves the dye but cannot swell into the polyethylene. Blue wicks are thereby formed without solvent or surface dye.

The coloured wick is then covered with a paste of glucose 201, dissolved in water and stirred carefully to remove large globules. The paste is then spread over the wick and left to set overnight. An substantially opaque layer of glucose is formed, obscuring the wick.

When the wick is then added to urine (or any other aqueous sample), the glucose paste layer dissolves, revealing the coloured wick.

EXAMPLE 4.1

As with example 4.0, a coloured wick 300, illustrated schematically in FIG. 3, is formed. It is covered with white Whatman No. 1 filter paper 301 which obscures the colour of the wick when dry but which, when wet, is translucent allowing the underlying coloured wick to become apparent, providing a visual indication that wetting has taken place. (Whatman is a registered trade mark).

Alternative materials which are opaque when dry but at least partially transparent when wet can be used including, for example, nylon microporous membranes such as Novylon® L-series nylon 6,6 membranes available from Cuno Inc., Meridien, Conn., USA; or nitrocellulose membranes with or without a clear laminate backing as are available from Millipore Corporation, Bedford, Mass., USA or Schleicher & Schuell GmbH of Dassel, Germany.

EXAMPLE 4.2

With reference to FIG. 4, a strip of acetate 402 has wording printed thereon, for example, the name of the product or a message indicating that the product has been used correctly. The acetate layer is stuck to a surface of the wick 400; for example, with a glue. The acetate layer is then obscured with glucose paste or filter paper 404 as in examples 4.0 and 4.1.

A benefit of this configuration is that acetate can readily be decorated with plain colours, patterns, writing, symbols or logos and that, as it is a separate layer to the wick, it minimises changes to the wicking properties of the wick.

EXAMPLE 5

A colour changing means may be applied as a label on one or both surfaces of the wick. A suitable label is a standard pH paper using an indicator system as discussed above. Standard pH papers have indicators immobilised in a fashion in which they will not leach, which prevents interference with the assay carried out by the assay device or alteration of the wicking properties.

BDH indicator strips, pH range 0 to 6 were purchased from Merck Ltd., Lutterworth, Leicestershire and a pale green square was acidified using a few drops of 0.1M HCl forming a pale yellow colour which was retained when the square was dried in warm air. The square was then cut out and removed from its plastic backing in order that it could be placed in fluid communication with the wick and then stuck to the wick with Pritt® stick or another adhesive. Upon addition of water, Tris buffer previously dried into the wick pushes the pH in the wick above 6.0 and the square of indicator paper changes from a pale yellow to a blue/green colour.

Alternatively the covered acetate layer of example 4.0 may be used as a label or other colour revealing/colour changing labels my be applied.

EXAMPLE 6

The polymer/colour changing compounds discussed above can be immobilised in a band, stripe or other pattern on the wick rather than colouring the entire wick by applying the polymer/colour changing compound mixture selectively to specific parts of the wick.

The invention claimed is:

1. An assay device for determining whether at least one analyte of interest is present in a liquid sample; the device comprising:
    a reaction zone in which a reagent can react with the analyte of interest; and
    a bibulous member located upstream of the reaction zone which, when contacted with the liquid sample, draws liquid therefrom towards the reaction zone; the bibulous member being formed of bicomponent fibers and comprising an indicator different from the reagent, the indicator changing to an indicator color when the bibulous member is wetted by the liquid of the sample to indicate the presence of liquid contact to the bibulous member, the indicator changing to the indicator color independent of the presence of analyte in the liquid; and wherein the indicator comprises a chemical species that changes color in response to an inherent property of the liquid sample.

2. An assay device as claimed in claim 1 wherein the chemical species is a pH indicator.

3. An assay device as claimed in claim 1 wherein the chemical species comprises two or more dyes together forming a screened indicator.

4. An assay device as claimed in claim 1 wherein the chemical species is a chromoreactand.

5. An assay device as claimed in claim 1 wherein the chemical species is a solvatochromic dye.

6. An assay device as claimed in claim 1 wherein the chemical species is immobilised within a polymer.

7. An assay device according to claim 1 wherein the indicator comprises a pH paper in fluid contact with the bibulous member.

8. An assay device as claimed in claim 1, wherein the liquid sample is urine and the at least one analyte is hCG.

9. An assay device as claimed in claim 1, wherein the liquid sample is urine and the at least one analyte is a drug of abuse.

10. An assay device according to claim 1, the device being adapted to co-operate with a measuring device.

11. An assay device according to claim 1, further comprising a hollow casing constructed of moisture-impervious solid material and containing a dry porous carrier which communicates directly or indirectly with the exterior of the casing such that a liquid sample can be applied to the porous carrier, the device also containing a labelled specific binding reagent for an analyte which labelled specific binding reagent is freely mobile within the porous carrier when in the moist state, and unlabelled specific binding reagent for the same analyte which unlabelled reagent is permanently immobilised in a detection zone on the porous carrier and is therefore not mobile in the moist state, the relative positioning of the labelled reagent and detection zone being such that the liquid sample applied to the device can pick up labelled reagent and thereafter permeate into the detection zone, the device incorporating means enabling the extent (if any) to which the labelled reagent becomes bound in the detection zone to be observed.

12. An assay device according to claim 1, wherein the indicator is adapted to change colour when sufficient sample has been applied to the wick to generate a meaningful assay result.

13. An assay device according to claim 1, further comprising a positive control which indicates that not only has sufficient liquid been taken up, but that at least one additional aspect of the assay device has worked correctly.

14. An assay device according to claim 1, wherein the indicator causes the bibulous member change colour substantially immediately upon contact with the liquid sample.

15. An assay device according to claim 1, wherein the reagent comprises an antibody to the analyte.

16. An assay device according to claim 1, further comprising a casing containing the reaction zone and only partially containing the bibulous member.

17. An assay device according to claim 16, wherein the indicator causes substantially all of the bibulous member protruding from the casing to change color.

18. A method of determining the presence of at least one analyte in a liquid sample, the method comprising:

contacting an assay device in accordance with claim 1 with the liquid sample; and observing the assay result.

19. An assay device as claimed in claim 1, wherein the bicomponent fibers of the bibulous member have a core of polyester surrounded by a sheath of nylon.

* * * * *